US009671389B2

United States Patent
Van Kesteren

(10) Patent No.: US 9,671,389 B2
(45) Date of Patent: Jun. 6, 2017

(54) APPARATUS FOR MEASURING A LEVEL OF A SPECIFIC GAS IN EXHALED BREATH

(75) Inventor: Hans Willem Van Kesteren, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1384 days.

(21) Appl. No.: 13/503,669

(22) PCT Filed: Oct. 29, 2010

(86) PCT No.: PCT/IB2010/054912
§ 371 (c)(1),
(2), (4) Date: Jul. 13, 2012

(87) PCT Pub. No.: WO2011/055286
PCT Pub. Date: May 12, 2011

(65) Prior Publication Data
US 2012/0271188 A1 Oct. 25, 2012

(30) Foreign Application Priority Data
Nov. 3, 2009 (EP) ..................................... 09174836

(51) Int. Cl.
*A61B 5/08* (2006.01)
*G01N 33/497* (2006.01)
(Continued)

(52) U.S. Cl.
CPC ......... *G01N 33/497* (2013.01); *A61B 5/0095* (2013.01); *A61B 5/082* (2013.01);
(Continued)

(58) Field of Classification Search
CPC .................. A61B 5/082; A61B 5/0095; G01N 2021/1704; G01N 29/2418; G01N 33/497;
(Continued)

(56) References Cited

U.S. PATENT DOCUMENTS 5,645,071 A * 7/1997 Harnoncourt et al. ....... 600/532
6,618,148 B1   9/2003 Pilgrim et al.
(Continued)

FOREIGN PATENT DOCUMENTS

CH   685889    10/1995
CN   1721824 A  1/2006
(Continued)

OTHER PUBLICATIONS

G. Zhang, "Detection of Air Pollutant NO2 and the Measurement of Sound Velocity by Laser-Induced Photoacoustic, 2008 International Conference on Optical Instruments and Technology: Advanced Sensor Technologies and Applications", Proc. of SPIE vol. 7157, pp. 71571G-1-71571G-7.

*Primary Examiner* — Navin Natnithithadha
*Assistant Examiner* — Meredith Weare
(74) *Attorney, Agent, or Firm* — Michael W. Haas

(57) ABSTRACT

There is provided an apparatus for measuring levels of a specified gas in exhaled breath, the apparatus comprising a photoacoustic sensor for providing a measurement representative of the level of the specified gas in the exhaled air, wherein the photoacoustic sensor comprises a light source that is modulated at a first frequency; a sound speed measurement module for measuring the sound speed of the exhaled breath, wherein the sound speed measurement module operates either at a second frequency that is substantially different to the first frequency or in a pulsed mode; wherein the first frequency of the modulated light source is adjusted during exhalation in accordance with the measured speed of sound of the exhaled breath.

12 Claims, 3 Drawing Sheets

(51) Int. Cl.
*A61B 5/00* (2006.01)
*G01H 5/00* (2006.01)
*G01N 21/17* (2006.01)
*G01N 29/024* (2006.01)
*G01N 29/24* (2006.01)
*G01N 29/34* (2006.01)

(52) U.S. Cl.
CPC ............ *G01H 5/00* (2013.01); *G01N 21/1702* (2013.01); *G01N 29/024* (2013.01); *G01N 29/2425* (2013.01); *G01N 29/348* (2013.01); *G01N 2021/1704* (2013.01); *G01N 2291/0215* (2013.01); *G01N 2291/02809* (2013.01)

(58) Field of Classification Search
CPC ............ G01N 29/024; G01N 21/1702; G01N 29/2425; G01N 29/348; G01N 2291/02809; G01N 2291/0215; G01H 5/00
See application file for complete search history.

(56) References Cited

U.S. PATENT DOCUMENTS

| | | | |
|---|---|---|---|
| 6,691,582 B1 | 2/2004 | Nawa | |
| 7,004,909 B1* | 2/2006 | Patel et al. | 600/532 |
| 7,101,340 B1* | 9/2006 | Braun | 600/532 |
| 7,635,339 B2* | 12/2009 | Harnoncourt et al. | 600/532 |
| 8,312,758 B2* | 11/2012 | Tobias | 73/24.02 |
| 8,322,190 B2* | 12/2012 | Kalkman | A61B 5/0095 |
| | | | 73/24.02 |
| 2003/0208133 A1* | 11/2003 | Mault | 600/532 |
| 2003/0229290 A1* | 12/2003 | George et al. | 600/532 |
| 2007/0191726 A1* | 8/2007 | Harnoncourt et al. | 600/532 |
| 2008/0011055 A1* | 1/2008 | Riddle | 73/24.02 |
| 2008/0134756 A1* | 6/2008 | Riddle | 73/24.02 |
| 2009/0128819 A1* | 5/2009 | Van Kesteren et al. | 356/437 |
| 2009/0229345 A1* | 9/2009 | Van Kesteren | 73/24.02 |
| 2009/0288474 A1* | 11/2009 | Kalkman | A61B 5/0095 |
| | | | 73/24.02 |
| 2010/0147051 A1* | 6/2010 | Tobias | 73/24.02 |
| 2010/0192669 A1* | 8/2010 | Presura et al. | 73/23.3 |

FOREIGN PATENT DOCUMENTS

| | | | | |
|---|---|---|---|---|
| CN | 1091086475 A | 12/2007 | | |
| CN | 101506644 A | 8/2009 | | |
| DE | 102006020721 A1 | 11/2007 | | |
| JP | 05154113 A | 6/1993 | | |
| JP | 2004085421 A | 3/2004 | | |
| JP | 2004317459 A | 11/2004 | | |
| JP | 2008532036 A | 8/2008 | | |
| JP | 2008234019 A | 10/2008 | | |
| WO | WO 2006072867 A1 * | 7/2006 | ............ | G01N 21/17 |
| WO | WO 2006092751 A1 * | 9/2006 | ............ | G01N 21/17 |
| WO | WO 2006114766 A2 * | 11/2006 | ............ | G01N 21/17 |
| WO | WO2008026146 A1 | 3/2008 | | |
| WO | WO 2009001275 A1 * | 12/2008 | ........... | G01N 33/497 |
| WO | WO 2009007875 A2 * | 1/2009 | ............ | G01N 21/17 |

* cited by examiner

APPARATUS FOR MEASURING A LEVEL OF A SPECIFIC GAS IN EXHALED BREATH

TECHNICAL FIELD OF THE INVENTION

The invention relates to a method and apparatus for measuring the levels of a specific gas in exhaled breath.

BACKGROUND OF THE INVENTION

It is known that the concentration of nitric oxide (NO) in exhaled air can be used as an indicator of various pathological conditions. For instance, the concentration of exhaled nitric oxide (eNO) is a non-invasive marker for airway inflammation. Inflammation of the airways is typically present in people with asthma and monitoring for high concentrations of eNO can be used in a test which is useful in identifying asthma. Furthermore, measurements of eNO can be used for monitoring the effectiveness of inhaled corticosteroids (ICS) and in anti-inflammatory asthma management to titrate ICS dosage.

The standardized method of measuring eNO requires a single exhalation test at a fixed flow rate of 50 ml/s at an overpressure of at least 5 cm $H_2O$. The exhalation test requires a constant exhalation flow for a given period of at least 10 seconds, and is not simple to perform by those with breathing difficulties or by young children. Therefore, conventional devices make use of visual and acoustic feedback signals to guide the user through the test successfully. Commercially available systems from Aerocrine and Apieron have received U.S. FDA approval for standardized eNO measurements in children aged 7-18 years and adults under supervision of a trained operator in a physician's office. No FDA-approved system for young children is currently available.

It is clear that a more straightforward and natural breathing procedure (for example tidal breathing) would be more preferable for young children and for non-professional (i.e. home) use.

It has been proposed in EP application no. 09166814.5 to measure the flow rate and eNO during an exhalation and subsequently analyze the measured data using a model that describes the generation and transport of NO in the airway system. In this way, flow-independent parameters can be deduced from tidal breathing patterns and if necessary, the value at 50 ml/s used in the standardized method can be derived.

An apparatus has been developed that measures eNO with a $NO$-to-$NO_2$ (nitric oxide to nitrogen dioxide) converter and a photoacoustic sensor for $NO_2$. The latter has been described in "Relaxation effects and high sensitivity photoacoustic detection of $NO_2$ with a blue laser diode" by Kalkman and Van Kesteren in Applied Physics B 90 (2008) p 197-200. This apparatus enables, in combination with a $NO$-to-$NO_2$ converter, a detection limit of NO in the low parts-per-billion (ppb) range and a real-time measurement of the NO concentration as required for tidal breathing, but an acoustic resonator with a high quality factor is required as part of the photoacoustic sensor in order to reach this detection limit.

However, during tidal breathing, the concentrations of $O_2$ and $CO_2$ in the exhaled breath change and this results in a change in the speed of sound of the exhaled air. The related shift of the resonance frequency of the acoustic resonator leads to a variation in the response to NO during the exhalation.

In a paper entitled "Photoacoustic spectrometer for measuring light absorption by aerosol: instrument description" by Arnott et al. [Atmospheric Environment 33 (1999) p 2845-2852] a photoacoustic spectrometer is described which incorporates a piezoelectric disk for sound generation that can be used to determine the resonance frequency of the photoacoustic cell. This spectrometer could either be operated in a mode to determine the resonance frequency with the piezoelectric disk or be operated in a photoacoustic gas sensing mode with the light source being modulated at a fixed frequency and the piezoelectric disk switched off. For environmental air with a slowly varying composition and temperature this approach works satisfactory. However, as with the previously-described apparatus, this photoacoustic spectrometer cannot adapt to the shift of the resonance frequency that occurs during exhalation due to changes in concentration of $O_2$ and $CO_2$.

In principle the photoacoustic sensor can be operated at various modes of the acoustic resonator and non-interfering longitudinal and transverse modes can be chosen for photoacoustic sensing and resonance tracking. In practice, the involvement of longitudinal as well as transverse modes leads to large resonator sizes and a significant loss of sensitivity.

SUMMARY OF THE INVENTION

Therefore, there is a need for an improved apparatus that overcomes this problem with measurements of NO and other specific gases in exhaled breath. Furthermore, it would be advantageous if the sensor module for NO detection in exhaled breath provides the NO concentration in combination with flow and molar mass of the gas mixture to enable an accurate analysis of the NO production and transport in the airways.

There is therefore provided an apparatus for measuring levels of a specified gas in exhaled breath, the apparatus comprising a photoacoustic sensor for providing a measurement representative of the level of the specified gas in the exhaled air, wherein the photoacoustic sensor comprises a light source that is modulated at a first frequency; a sound speed measurement module for measuring the sound speed of the exhaled breath; wherein the first frequency of the modulated light source is adjusted during exhalation in accordance with the measured speed of sound of the exhaled breath.

According to a second aspect of the invention there is provided a method of measuring levels of a specified gas in exhaled breath, the method comprising measuring the speed of sound of the exhaled breath; adjusting a modulation frequency of a light source in a photoacoustic sensor during exhalation in accordance with the speed of sound of the exhaled breath; and using the photoacoustic sensor to provide a measurement representative of the level of the specified gas in the exhaled breath.

BRIEF DESCRIPTION OF THE DRAWINGS

Embodiments of the invention will now be described in more detail, by way of example only, with reference to the following drawings, in which.

DETAILED DESCRIPTION OF THE PREFERRED EMBODIMENTS

Figure 1:
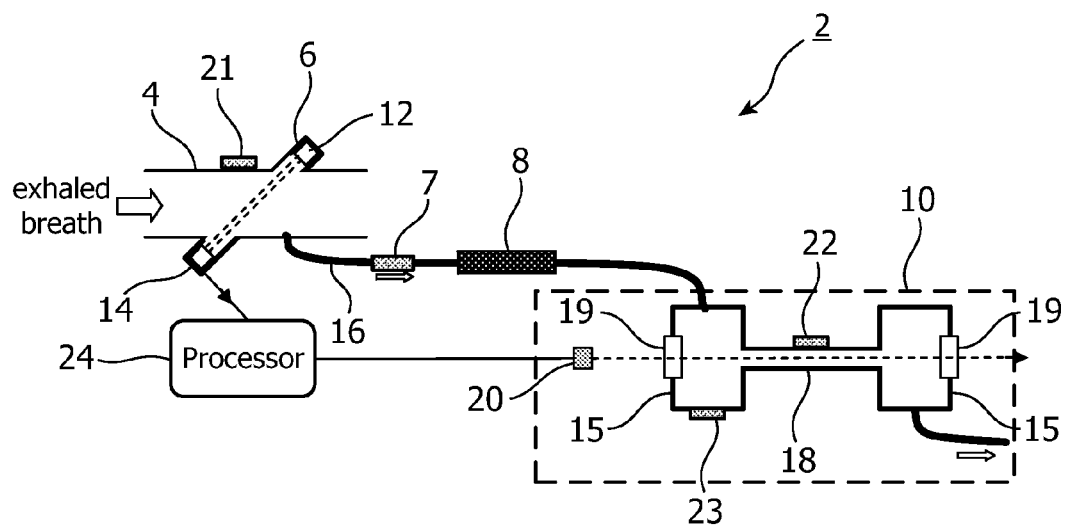
FIG. 1 is a block diagram of an apparatus in accordance with a first embodiment of the invention.

A first embodiment of the apparatus for measuring exhaled nitric oxide (NO) levels according to the invention is shown in FIG. 1. The apparatus 2 comprises a breathing tube or mask 4 into which a patient exhales, a sound speed measurement module 6 located in the breathing tube 4, a humidity reduction unit 7, a nitric oxide to nitrogen dioxide ($NO_2$) converter 8 for converting the nitric oxide in a small measurement sample of the exhaled breath into nitrogen dioxide, and a photoacoustic sensor 10 that measures the level of nitrogen dioxide in the measurement sample.

The sound speed measurement module 6 preferably operates in the ultrasound frequency range (i.e. typically between 20 kHz and 200 kHz) and measures transit-times of sound pulses between a pair of transducers 12, 14 along and against the direction of flow of the exhaled breath. The flow is derived from the difference in transit times and is independent of the gas composition (i.e. is not affected by changes in concentration of oxygen and carbon dioxide). During tidal breathing, the sound speed measurement module 6 allows the apparatus 2 to take account of the flow dependent NO production in the airways of the patient.

The sum of the ultrasonic pulse transit times between the two transducers 12, 14 is used to derive the speed of sound of the exhaled gas mixture, and this information is used to adjust a frequency of the photoacoustic sensor 10. This significantly improves the accuracy of eNO detection during tidal breathing. In combination with the temperature of the exhaled breath which is reasonably well known, the molar mass of the exhaled breath can also be derived from the sum of the ultrasonic pulse transit times. For a higher accuracy a temperature sensor 21 can be incorporated in the breathing tube 4. The shape of the molar mass pattern during exhalation, being similar to a capnogram, provides information on $CO_2/O_2$ gas exchange and obstruction in the respiratory tract which can be taken into account in the analysis of the flow dependent NO production in the airways as described in EP application no. 07111132.2.

In the illustrated embodiment, the pair of transducers 12, 14 are arranged at a non-zero angle to a plane that is perpendicular to the direction in which the exhaled air passes through the apparatus 2. In other words, the transducers 12, 14 emit ultrasonic pulses at an angle across the direction of flow of exhaled breath.

Each of the transducers 12, 14 operate as a transmitter as well as a receiver to enable the measurement of the transit times of short ultrasound pulses in both directions across the exhaled air flow.

Part of the exhaled breath passing through the tube 4 is separated into a side stream 16 to provide the measurement sample which is passed to the humidity reduction unit 7 and NO to $NO_2$ converter 8. Depending on the material and composition of the converter, typically 80 to 100% of the NO is converted into $NO_2$. After the converter 8, the measurement sample (with $NO_2$) is passed into the photoacoustic sensor 10 which determines the $NO_2$ concentration.

The photoacoustic sensor 10 comprises a resonator tube 18 that operates in a longitudinal plane wave mode and has a resonant frequency, $f_r$, a laser 20 that generates a laser beam that is passed through a window 19 and buffer volume 15 to the measurement sample in the resonator tube 18. A microphone 22 records the intensity of the sound generated by the laser beam passing through the measurement sample. The laser 20 generates a laser beam that has a wavelength within the absorption range of $NO_2$, and the intensity of the laser beam is modulated at a frequency that substantially corresponds to the resonant frequency $f_r$ of the resonator tube 18. The periodic absorption of optical energy and subsequent release of thermal energy leads to pressure variations that are picked-up by the microphone 22. Synchronous detection of the microphone signal at the laser modulation frequency results in a signal proportional to the $NO_2$ concentration. The optimal dimensions and thereby the resonant frequency $f_r$ of the resonator tube 18 depends on many factors, such as the relaxation dynamics of the gas being detected, spectral noise behavior of the microphone 22, interfering noise sources, etc. Typically, the resonant frequency $f_r$ is a frequency from a few hundred Hz to a few kHz. Where the photoacoustic sensor 10 is used for detecting levels of $NO_2$, the resonance frequency can for instance be at 5 kHz.

Preferably, the sound speed measurement module 6 operates at a frequency that is substantially different to the resonant frequency of the resonator tube 18 (or the sound speed measurement module 6 operates in a pulsed mode).

As indicated in the Background section, the spectral bandwidth of a photoacoustic resonator is described by a quality factor, and the quality factor is equal to the resonant frequency, $f_r$, divided by the bandwidth. Typical quality factors for photoacoustic resonators are in the range 5 to 50. In one embodiment, the frequency at which the sound speed measurement module 6 operates is substantially different to the resonant frequency of the resonator tube 18 if the frequency at which the sound speed measurement module 6 operates deviates by more than 5 times the bandwidth from the resonant frequency, $f_r$, of the photoacoustic sensor 10.

This allows the measurements of the sound speed to be made at the same time, or substantially at the same time, that the photoacoustic sensor 10 analyses the measurement sample (i.e. both measurements can be carried out during normal breathing by the subject). For example, the frequency used by the sound speed measurement module 6 can be in the range of tens of kHz to MHz, as these high frequencies enable accurate transit time measurements over small distances and do not interfere with acoustic resonance that is at a few kHz or few hundred Hz.

Where the sound speed measurement module 6 operates in a pulsed mode, a typical pulse could be two cycles of a 100 kHz wave. Again, for $NO_2$ detection, the resonant frequency can be 5 kHz.

As described above in the Background section, the quality factor of the resonator tube 18 is preferably high to enable accurate detection of $NO_2$ concentrations in the low parts-per-billion (ppb) range. However, the high quality factor makes the apparatus 2 more sensitive to variations in the main constituents of exhaled breath like $O_2$ and $CO_2$, and these do vary during tidal breathing.

Therefore, a processor 24 is provided that is connected to the sound speed measurement module 6 to receive the pulse transit times, derive from the difference in the ultrasound transit times from each of the transducers 12, 14 to the other the magnitude of the exhalation flow and from the sum of the transit times the sound speed for the exhaled breath mixture. The exhalation flow is used in combination with the exhaled NO level to derive one or more flow-independent parameters describing the NO production and transport in the airways.

The processor 24 uses the sound speed for the exhaled breath to derive a control signal for the laser 20 in the photoacoustic sensor 10. The control signal is used to fine tune the modulation frequency of the laser 20 in the photoacoustic sensor 10. Preferably the modulation frequency of the laser 20 in the photoacoustic sensor 10 is adjusted continuously or regularly during the breathing cycle. Changes in sound speed and resonance frequency are coupled because the resonator tube 18 has a fixed length. So for an optimal performance of the photoacoustic sensor the resonance frequency and thus the laser modulation frequency have to be adjusted to changes in the gas composition.

It will be appreciated that there will be differences in the temperature and humidity of the exhaled air in the breathing tube 4 close to the sound speed measurement module 6 and the exhaled air in the measurement sample in the photoacoustic sensor 10. Furthermore, the sound speed measured in the ultrasound frequency range can deviate slightly from the sound speed relevant at the resonance frequency of the photoacoustic sensor 10. In a fixed apparatus 2, i.e. where the distance between and the respective arrangement of the sound speed measurement module 6 and the photoacoustic sensor 10 is fixed, the temperature difference can be determined separately (perhaps in a calibration test) and a correction constant can be set in the processor 24 to compensate for the aforementioned effects. In an alternative approach, temperature sensors 21 and 23 are incorporated in the breathing tube 4 and photoacoustic sensor 10 respectively. Because the dependence of sound speed on temperature is known, the sound speed can be accurately compensated for the temperature difference. The effect of the humidity difference on the sound speed is much smaller than the effect of the temperature difference so generally it will not be necessary to compensate for this effect. The humidity of the exhaled air is close to saturation while the humidity reduction unit 7 reduces the humidity in a known way so the humidity difference is known and the sound speed can be compensated for this difference if necessary. Differences in sound speed due to differences in sound frequency applied in the photoacoustic sensor 10 and in the sound speed measurement module 6 will generally be negligible when the ultrasound sensor is operated at frequencies below 100 kHz.

Moreover, depending on the specific length of and flow in the side stream 16, there can be a small time delay between the sound speed measurement module 6 measurement and the photoacoustic sensor 10 measurement. The processor 24 can be configured to take this time delay into account.

Figure 2:
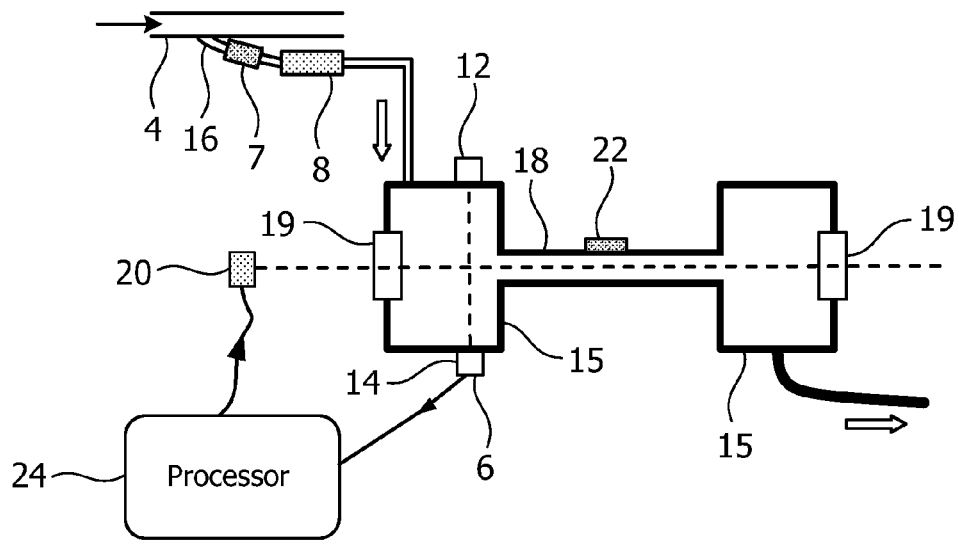
FIG. 2 is a block diagram of an apparatus in accordance with a second embodiment of the invention.

In an alternative embodiment of the invention shown in FIG. 2, the sound speed measurement module 6 based on an ultrasonic transit time measurement and the photoacoustic sensor 10 can be combined into a single device. In particular, the transit time sensor 6 can be incorporated into the buffer chamber 15 which enables accurate detection of the sound speed from the measurement sample. This combination is possible because the sound speed measurement module 6 operates at frequencies in the tens of kHz to MHz range, and these high frequencies enable accurate transit time measurements over small distances and do not interfere with the acoustic resonance at a few kHz or few hundred Hz (i.e. as in the embodiment above, the sound speed measurement module 6 operates in a frequency range that is substantially different to the frequency range in which the resonant frequency of the resonator tube 18 lies (or the sound speed measurement module 6 operates in a pulsed mode)).

Figure 3:
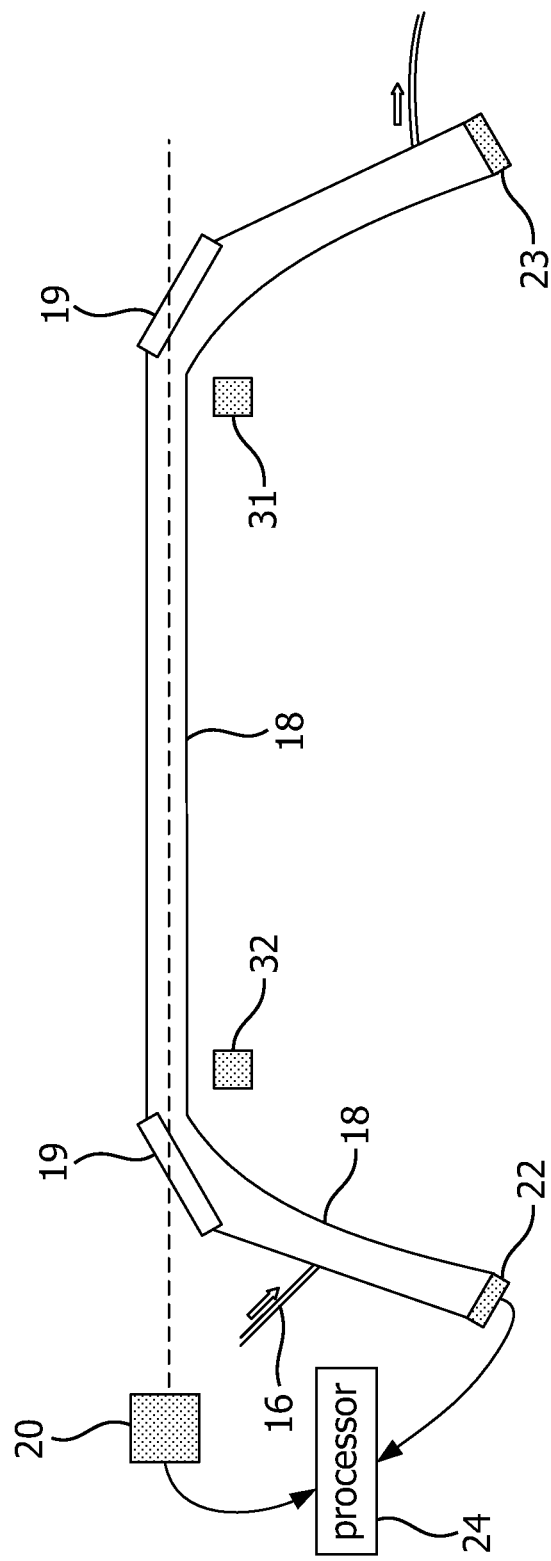
FIG. 3 is a block diagram of an apparatus in accordance with a third embodiment of the invention.

A third embodiment is shown in FIG. 3. The photoacoustic cell is made of a transparent material, for instance glass, has a resonator chamber 18 operating at a resonance frequency $f_r$ with acoustic pressure nodes around the position of the windows 19 and a pressure antinodes at the position of the microphone 22 and in the middle between the windows. The sound speed measurement module consists of two anti-phase modulated light sources 31 and 32 (for instance two LED's) and the microphone 22 to pick up the generated sound signal. The sound is generated by partial absorption of the light in the wall of the resonator chamber 18 and thermal coupling with the gas inside the resonator chamber 18. The sound speed measurement module makes use of a special longitudinal resonance of the photoacoustic cell at a frequency close to ½ $f_r$. This mode does not interfere with the mode at $f_r$ because it is only excited by anti-phase pressure antinodes excited by the anti-phase modulated light sources 31 and 32. The laser beam with a substantially constant power distribution over the cell length will not excite this mode. The sound speed is derived from the modulation frequency of light sources 31, 32 yielding a maximum microphone signal. A processor 24 calculates on basis of this signal the resonance frequency $f_r$ and adjusts the laser modulation frequency accordingly. The wavelength of the LED sources 31, 32 is not critical because of the generally broad absorption feature of the photoacoustic cell wall. The sound speed derived from the optimum modulation frequency of the light sources 31, 32 together with the temperature of the gas mixture determined by temperature sensor 23 will yield the molar mass of the gas sample in the photoacoustic cell. In one particular implementation of this embodiment, the resonant frequency for $NO_2$ detection is 5 kHz, the frequency at which the sound speed measurement module 6 operates at a frequency of 2.5 kHz, and the quality factor of the photoacoustic sensor 10 is 20.

In implementations of the invention where the apparatus 2 is for use in detecting levels of specific gases other than NO, the laser 20 is configured to generate a laser beam having a wavelength within the absorption range of that specific gas. Moreover, the converter 8 can be modified or omitted as appropriate depending on the specific gas in the exhaled breath to be measured.

Figure 4:
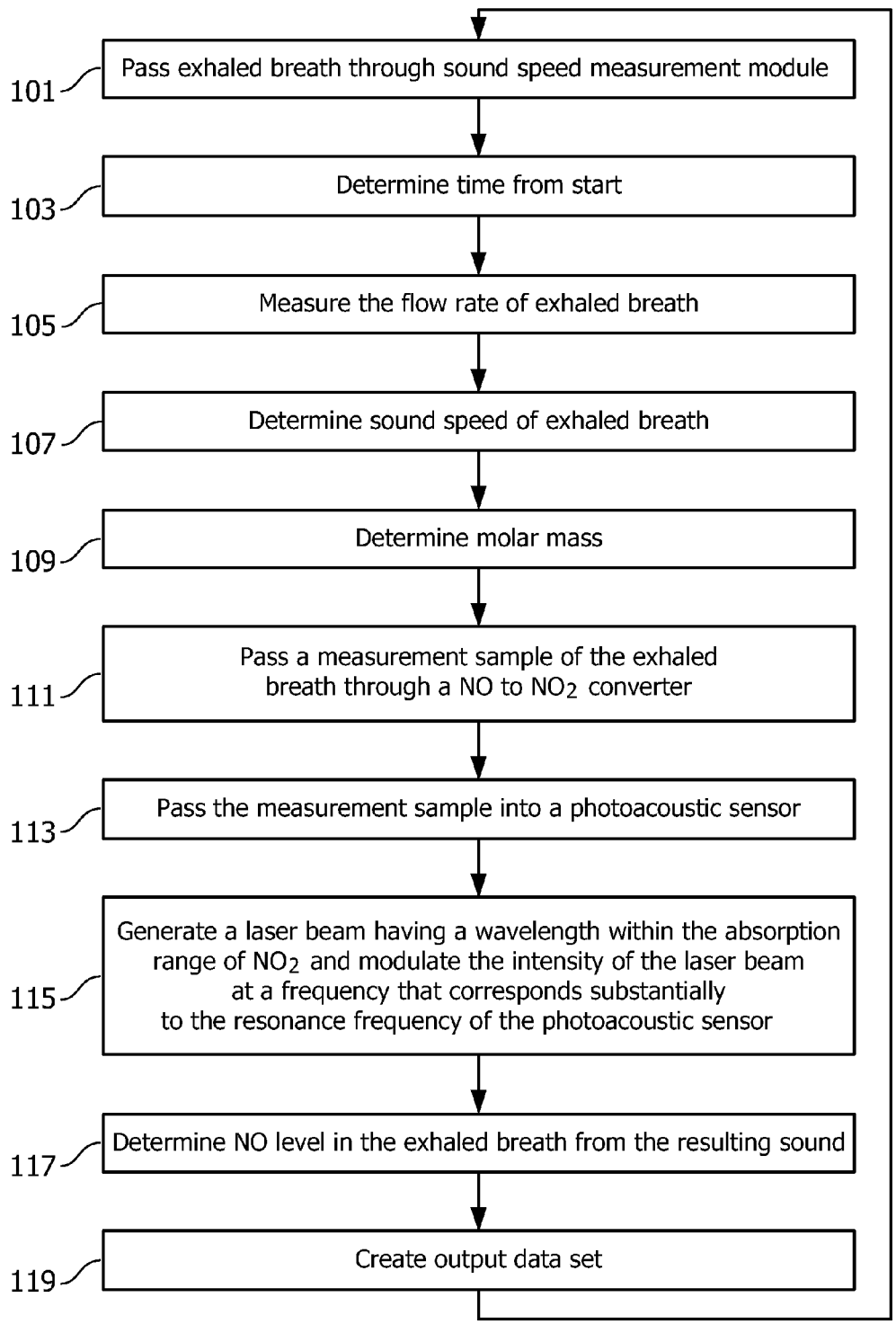
FIG. 4 is a flow chart illustrating a method in accordance with the invention.

A method of determining nitric oxide levels in exhaled breath according to the invention is shown in FIG. 4. In step 101, an exhaled breath sample passes through the sound speed measurement module 6. Then, in step 103 the time is determined from the start of the measurement procedure.

Then, in step 105, the flow rate of the exhaled breath is measured, preferably using an ultrasonic flow sensor 6 as described above.

In step 107, the speed of sound of the exhaled breath is determined.

In step 109, the molar mass is determined from the transit times and temperature of the exhaled breath sample.

In step 111, a measurement sample of the exhaled breath sample is passed through a humidity reduction unit 7, a NO to $NO_2$ converter 8 and the resulting sample is passed into a resonator chamber 18 of a photoacoustic sensor 10 (step 113).

In step 115, a laser beam is generated having a wavelength within the absorption range of $NO_2$ and the intensity of the laser beam is modulated at a frequency that substantially corresponds to the resonance frequency of the photoacoustic sensor 10 which is determined from the speed of sound of the breath sample, taking into account correction factors to the sound speed and gas transport time in the side stream sample line 16.

In step 117, the NO level in the exhaled breath is determined from the measured sound using the instrument constants for the microphone output per concentration unit of $NO_2$ and conversion ratio of $NO_2$ to NO for the converter 8.

Finally, in step 119 an output data set is created combining the NO concentration and corresponding flow, molar mass and time from the start of the measurement.

The method then returns to step 101 and repeats the data generation for a time frame. It will be appreciated that as the method is for use during tidal breathing, the method therefore repeats continuously.

All the output data sets for one or multiple exhalations generated according to this method form the inputs for an analysis module that extracts one or more parameters describing the NO production and gas transport in the airways. These in turn provide a measure of the airway inflammation either or not in combination with information on an obstruction in the airways.

There is therefore provided an improved apparatus for measuring levels of a specific gas, and particularly nitric oxide, in exhaled breath.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for measuring levels of a specified gas in breath exhaled by a subject, the apparatus comprising:
    a photoacoustic sensor for providing a measurement representative of the level of the specified gas in the exhaled breath, wherein the photoacoustic sensor comprises a light source that is modulated at a first frequency; and
    a sound speed measurement module for measuring the sound speed of the exhaled breath, wherein the sound speed measurement module operates either at a second frequency that is substantially different to the first frequency or in a pulsed mode;
    wherein the sound speed measurement module comprises a second light source and a third light source which are anti-phase modulated; and
    wherein the first frequency of the modulated light source is adjusted during exhalation in accordance with the measured speed of sound of the exhaled breath.

2. An apparatus as claimed in claim 1, wherein the photoacoustic sensor comprises a resonator chamber that is operated in a plane wave mode, and wherein the first frequency of the modulated light source is adjusted in accordance with the measured speed of sound of the exhaled breath and an acoustic mode of the resonator chamber.

3. An apparatus as claimed in claim 1, wherein the sound speed measurement module operates at the second frequency.

4. An apparatus as claimed in claim 1, wherein the sound speed measurement module comprises:
    wherein the apparatus is configured to provide a measurement of the specified gas and exhalation flow.

5. An apparatus as claimed in claim 1, wherein sound speed measurement module comprises:
    a temperature sensor for determining the temperature of the specified gas; and
    a processor for determining the sound speed in the exhaled breath and a molar mass from at least the temperature; and wherein the apparatus is configured to provide a measurement of the specified gas and the molar mass.

6. An apparatus as claimed in claim 1, wherein the specified gas is nitric oxide.

7. An apparatus as claimed in claim 6, wherein the apparatus further comprises a converter for converting nitric oxide in the exhaled breath to nitrogen dioxide to provide a measurement sample, and wherein the photoacoustic sensor measures the levels of nitrogen dioxide in the measurement sample, the measured levels of nitrogen dioxide corresponding to the levels of nitric oxide in the exhaled breath.

8. An apparatus as claimed in claim 6, wherein the apparatus further comprises a processing unit for determining one or more parameters describing nitric oxide production in the subject's airways based on the exhaled nitric oxide and flow patterns during one or more exhalations.

9. An apparatus as claimed in claim 6, wherein the apparatus further comprises a processing unit for determining one or more parameters describing nitric oxide production in the subject's airways based on the exhaled nitric oxide, flow and molar mass patterns during one or more exhalations.

10. A method of measuring levels of a specified gas in exhaled breath using a photoacoustic sensor comprising a first light source modulated at a first frequency, and a sound speed measurement module comprising a second light source and a third light source which are anti-phase modulated, the method comprising:
    measuring the speed of sound of the exhaled breath, with the sound speed measurement module;
    adjusting the first frequency during exhalation in accordance with the speed of sound of the exhaled breath; and
    using the photoacoustic sensor to provide a measurement representative of the level of the specified gas in the exhaled breath;
    wherein the speed of sound is measured either at a second frequency that is substantially different to the first frequency or in a pulsed mode.

11. A method as claimed in claim 10, wherein the photoacoustic sensor provides a measurement representative of the level of the specified gas in the exhaled breath by:
    passing light from the first light source through a measurement sample of the exhaled breath that is contained in a resonance chamber of the photoacoustic sensor, the light from the first light source having a wavelength in the absorption range of the specified gas; and
    measuring the sound generated from the laser beam passing through the measurement sample of the exhaled breath to provide the measurement representative of the specified gas in the exhaled breath.

12. A method as claimed in claim 10, wherein the specified gas is nitric oxide and wherein the method further comprises the step of:

passing a sample of the exhaled breath through a nitric oxide to nitrogen dioxide converter to generate a measurement sample;

wherein the photoacoustic sensor measures the level of nitrogen dioxide in the measurement sample to provide the measurement representative of the level of nitric oxide in the exhaled breath.

* * * * *